United States Patent [19]

Davies

[11] Patent Number: 5,849,319
[45] Date of Patent: Dec. 15, 1998

[54] USES FOR STRIPPED SPENT SILVER CATALYSTS

[75] Inventor: Ronald F. Davies, Queensbury, N.Y.

[73] Assignee: Ames Goldsmith Corp., Glen Falls, N.Y.

[21] Appl. No.: 735,003

[22] Filed: Oct. 22, 1996

Related U.S. Application Data

[60] Provisional application No. 60/006,074 Oct. 24, 1995.
[51] Int. Cl.⁶ ..................................................... A01N 25/08
[52] U.S. Cl. ........................... 424/409; 424/404; 424/411; 424/412; 424/413; 424/414; 424/421; 424/618
[58] Field of Search ..................................... 424/618, 404, 424/405, 409, 411–415, 421

[56] References Cited

U.S. PATENT DOCUMENTS 4,608,247  8/1986  Heinig, Jr. ................................. 424/16

OTHER PUBLICATIONS

The 1995 Grolier Multimedia Encyclopedia, "Silver", 1995, Grolier Electronic Publishing, Inc.

*Primary Examiner*—Neil S. Levy
*Attorney, Agent, or Firm*—Marianne Fuierer; Howard M. Ellis

[57] ABSTRACT

Spent silver catalysts, from which the recoverable silver has already been stripped, was discovered to be useful for controlling microorganisms such as bacteria and fungi, including microorganisms in fluids such as water, or on surfaces to which coatings containing the stripped, spent silver catalysts are applied, and also in and on products in which the stripped, spent silver catalysts are incorporated.

20 Claims, No Drawings

USES FOR STRIPPED SPENT SILVER CATALYSTS

CROSS REFERENCE TO RELATED APPLICATION

This application claims the benefit of U.S. Provisional application Ser. No. 60/006,074, filed Oct. 24, 1995.

TECHNICAL FIELD

This invention generally relates to novel uses for the residue from spent silver based catalysts deposited on inert carriers which have been treated for reclaiming their silver values. More particularly, this invention relates to the discovery that this catalytic residue from silver stripping operations can used as broad spectrum biocides for controlling microorganisms, especially bacterial and fungal agents of disease.

BACKGROUND OF THE INVENTION

Silver shares Group 1B of the Period Table with gold, platinum and mercury and belongs to the family of noble metals. Silver has also been included in the group of metals referred to as precious metals, a distinction it shares with gold, platinum and palladium. Silver and its compounds are used in many fields, the most prominent of which are probably coinage and photography. However, silver and its compounds have a number of other uses as well.

Silver, for instance, is employed as a catalyst in several important chemical processes. For example, silver is utilized as a catalyst in the oxidation of ethylene to ethylene oxide. About 9.6 million metric tons of ethylene oxide were produced in 1992, a large increase over the 3.3 million tons produced in 1988, and the demand for ethylene oxide continues to grow.

Silver catalysts generally include three or four components. These components include a support material, the catalytically active silver, a promoter, and optionally, an inhibitor. Silver catalysts and specific components thereof are often proprietary.

Silver catalysts are generally supported. In the case of the catalysts used in the oxidation of ethylene to ethylene oxide, the support is a solid, inert material, capable of near continuous exposure to a temperature of about 250° C. to 300° C. in the presence of ethylene, air or oxygen, and ethylene oxide, as well as trace amounts of contaminants. Typical support materials include alumina, aluminosilicate and silicon carbide ceramics, zeolites, glass, and quartz. The support material is available in various, generally extruded shapes such as pellets, rings, grain, and so forth.

Catalytically active silver can be prepared by treating an aqueous silver salt solution with alkali; by thermal decomposition of silver salts, particularly silver carbonate, oxalate, or another silver salt of an organic acid; by reducing a silver salt with hydrogen, formaldehyde, hydrazine, or hydroxylamine; by the electrolysis of a solution of a silver salt; or by selectively removing secondary metals from a silver alloy.

The promoter in silver catalysts increases the activity and selectivity and enhances the longevity of the catalyst. The promoters are generally salts of alkali or alkaline earth metals, such as cesium, rubidium, potassium, calcium, or barium.

An inhibitor, or anti-catalyst, is sometimes present to suppress further oxidation of the ethylene oxide to carbon dioxide and water. Inhibitors present in the silver catalyst are generally alkali metal halides or cyanides. Alternatively, the inhibitor can be added to the vapor phase in which the oxidation takes place. Ethylene dichloride, ethylene dibromide, other alkyl halides, aromatic hydrocarbons, amines, and organometallic compounds can be used in this way.

The catalytically active silver, in combination with the promoter and the inhibitor, if present, are applied to the support material by coating the support with a suspension of these components in a fluid, by impregnating a porous support with the suspension, or by some functionally equivalent technique. The catalytically active silver generally comprises about 10–20 percent by weight of the finished silver catalyst.

In the catalytic oxidation of ethylene, the surface of the silver is thought to be covered with oxygen, and the catalyst may more properly be described as a silver oxide, rather than metallic silver. The understanding of the nature of the catalytic sites, the mechanisms by which the promoters and the inhibitors are effective, etc. is not complete, but such understanding is not required in order to practice the methods of this invention. Indeed, the methods can be practiced successfully regardless of the exact nature of the silver catalyst and the mechanism by which it functioned as a catalyst.

The aforesaid description illustrates the makeup of a silver catalyst employed in the production of one representative product, ethylene oxide, from one representative feedstock, i.e., ethylene. Silver catalysts employed in processes for taking other reactants to other products are similar but not identical to the silver catalysts described above. All such catalysts are regarded as being useful in the methods of this invention, however.

The life expectancy of the silver catalysts employed in the oxidation of ethylene to ethylene oxide typically is about 1–2 years. Factors which are known to affect the useful life of catalysts are the rate of ethylene feed over the catalyst and possible exposure of the catalyst to poisons, such as sulfur. Thus, the silver catalyst employed in the oxidation of ethylene must be replaced periodically. The same fate awaits similar silver catalysts employed in other processes.

It is generally possible to strip and recover the silver values from spent silver catalysts and recycle them. This stripping operation is typically accomplished by extracting or leaching the spent catalyst with an acid in which the silver is soluble, such as nitric acid, and then thoroughly washing the catalyst. The liberated silver metal can be recovered from aqueous solutions by methods well known to those skilled in the art.

Heretofore, after the silver was recovered, the residue, which was mostly the support material was usually discarded. Although some of the stripped, spent silver catalyst was incorporated into refractories and abrasives, these outlets consumed only a small fraction of the 5 million pounds of stripped, spent silver catalyst currently generated each year from the oxidation of ethylene alone.

This inventor has observed the chemical composition of a stripped, spent silver catalyst depends upon the manufacturer of the catalyst and the specific chemical process in which the catalyst was employed. However, in the typical stripped, spent silver catalyst, the alumina or other support material predominates, and the stripped, spent silver catalyst can be crushed and screened to produce a grain or powder of the particle size desired for the application at hand.

Since the stripped, spent silver catalysts are not biodegradable, the cost of land filling the material is quite high. Furthermore, land filling causes environmental concerns and potential liabilities to the landfill operator, as well as to the disposer. Thus, new beneficial uses for stripped, spent silver catalysts are needed.

SUMMARY OP THE INVENTION

Accordingly, it is the primary objective of this invention to provide a new use for stripped, spent silver catalysts which takes advantage of a previously unutilized and unrecognized useful characteristic, and therefore, unappreciated property of these materials. That is to say, this inventor, to the best of his knowledge, was the first to recognize and appreciate the presence of silver values remaining in stripped spent silver catalysts in sufficient concentration to impart a utility which is dependent on the presence of mere trace amounts of one component, namely silver, of the orginal multi-component catalytic composition of matter. As previously mentioned, heretofore stripped spent silver catalysts were used as refractory and abrasive materials, or alternatively, disposed of as landfill. Accordingly, this invention provides for novel and inventive new uses for stripped spent silver catalysts in methods for controlling microorganisms by contacting them with a biocidally effective amount of the stripped, spent silver catalyst. Since bulk quantities of stripped, spent silver catalysts are usually discarded, the methods of this invention have the advantage of a very economical means for controlling microorganisms while simultaneously reducing the environmental problems normally associated with the disposal (storage) of such materials.

It is a further objective of this invention to provide an inexpensive means for controlling potentially harmful microorganisms, e.g., bacteria, fungi, and so on, which may be present, for example, in fluids, such as the drinking water of a municipality, or water of uncertain purity in a remote location. The stripped, spent silver catalysts can be employed as broad spectrum biocides in swimming pools, hot tubs and other recreational bodies of water, or in other aqueous-containing systems. Representative examples of an aqueous system would include the decontamination of recirculating water in cooling towers or condensate from larger air conditioning systems. The methods are also applicable to the sterilization of effluents from sewage treatment facilities, including sludges, and contaminated effluents from manufacturing plants.

It is an additional objective of this invention to provide a method for protecting the surfaces of various articles against the growth of microorganisms thereon. It is yet another objective of the invention to extend the longevity of various products by incorporating stripped, spent silver catalyst therein.

As used herein, the term "stripped, spent silver catalyst" refers to the residue from supported silver catalysts described above from which the recoverable silver values have been removed. As applied to microorganisms, the term "control" means to decrease the concentration of the microorganisms, typically bacteria, fungi and possibly certain viruses by killing, degrading or preventing their reproduction. More generally, the term "microorganism" as used herein refers mainly to self-replicating microorganisms, such as bacteria and fungi, especially the infectious agents of disease which pose a threat in a biological system.

DETAILED DESCRIPTION OF THE INVENTION

This invention provides a method for controlling microorganisms which comprises contacting the microorganisms (or medium containing the microorganism) with a biocidally effective amount of a stripped, spent silver catalyst.

The amount of stripped, spent silver catalyst which is a biocidally effective amount will vary depending upon a number of factors. This inventor found that although substantially all of the silver values from the spent catalyst are removed in the stripping process, typically a trace amount, usually 0.1 percent by-weight, of silver remains in this residue, e.g., on the order of about 50–900 ppm of silver. The amount of silver depends upon the individual material. Further, it has been determined that the degree of biocidal activity of a stripped, spent silver catalyst is related to the amount of silver contained therein as the Examples which follow show. Consequently, the biocidally effective amount of stripped, spent silver catalyst will depend upon the silver content of the catalyst, a lesser amount of the stripped, spent silver catalyst being required to control a given concentration of microorganisms if the silver content is at the higher end of the range.

In addition, the amount of stripped, spent silver catalyst which is a biocidally effective amount will depend upon the length of time during which the microorganisms and the strippable, spent silver catalyst are in contact, a longer contact time requiring less of the stripped, spent silver catalyst. Also, some microorganisms are easier to control than are other microorganisms, so the biocidally effective amount will be less to control a susceptible microorganism than a resistant microorganism. The Examples which follow provide a base which is sufficient to provide an estimate of the biocidally effective amount for a given situation, but a certain amount of experimentation may be necessary to optimize the amount of stripped, spent silver catalyst to employ in a given situation.

For Examples 1–7, samples of seven stripped, spent silver catalysts were dried, crushed and evaluated for biological activity. The samples had been obtained from a variety of sources and were of unknown composition. Each of the samples was assayed for silver content by the procedure of EPA method SW 846 coupled with EPA method SW 846 7760A, and the samples were found to contain between about 400 and about 900 mg silver per kg as shown in Table 1 below.

The seven samples were evaluated for the their ability to control $E.coli$ and $E. faecium$ bacteria as follows:
Preparation of the Challenge Microorganisms $Escherichia\ coli$ (ATTC No. 11229), a gram negative bacterium, was subcultured onto standard plate count agar, and $Enterococcus\ faecium$ (ATTC No. 6569), a gram positive bacterium, was subcultured onto bile exculin azide agar the day before the biocide test. On the test day the cells were harvested by removing the growth from the agar surface using five milliliters of phosphate buffered water. The cells were centrifuged in sterile tubes to remove any media debris and the supernatant was transferred to a sterile container. The cell concentration was determined by the percent light transmission using a Genesys 5 spectrophotometer at 530 nm and compared with the laboratory database. The $E.coli$ transmission was adjusted to 88% and the $E.\ faecium$ to 85% to have approximately $2 \times 10^8$ cells per milliliter.
Biocide Test A cell suspension of ten milliliters of either $E.\ coli$ or $E.\ faecium$, with a cell density of $2 \times 10^6$ was prepared for each test material. The test material was weighed and added to the cell cultures. The tubes were mixed continuously for 30 minutes. At the end of the incubation time, 0.1 ml of the solution was added to 100 mls of sterile buffered water. From this dilution, 0.1 ml was removed and filtered through a 0.45 micron filter, then the remaining amount (99.9 mls) was filtered through another filter. The filters were put onto the culture media and incubated at 35.0±0.5 degrees C. for 22 to 24 hours. After incubation, the plates were counted and the percent reduction in cell concentration compared with the control.

Inoculum Control

A positive control was used to determine the cell density after the 30 minutes contact time. A post plate, negative control was used to show no cross-contamination and filtered at the end of the experiment.

The test data are shown in Table 1 below.

TABLE 1

Biocidal Screen of Stripped, Spent, Silver Catalyst Samples

| Sample | Grams of Sample (per 1 × $10^7$ cells) | Concentration of Silver (mg/kg) | E. Coli Percent Reduction | E. Faecium Percent Reduction |
| --- | --- | --- | --- | --- |
| A | 1.0 | 450 | 54.5% | 16.9% |
| B | 1.0 | 600 | 100% | 87.3% |
| C | 1.0 | 760 | 100% | 99.5% |
| D | 1.0 | 820 | 100% | 99.8% |
| E | 1.0 | 510 | 8.0% | 91.0% |
| F | 1.0 | 540 | 58.0% | 88.7% |
| G | 1.0 | 590 | 47.5% | 87.3% |

On the basis of the results in Examples 1–7, it is concluded that each of the seven stripped, spent silver catalysts exhibited the ability to control both gram positive and gram negative bacterial microorganisms.

Specific embodiments of the method of this invention are illustrated in the following Examples:

EXAMPLE 8

Stripped, Spent Silver Catalyst as a Water Treatment

Sterile, deionized water (1.0 liter) in an Erlenmeyer flask is contaminated with *E. faecium* at the level of $2 \times 10^6$ microorganisms per milliliter as determined by the spectrophotometric method, monitoring the transmission of the contaminated water at 530 nm, as described above. A 10 ml sample of the contaminated water is set aside. The dried, crushed, stripped, spent catalyst of Example 2 (10 g) is added to the remainder of the contaminated water, and the mixture is stirred for 0.5 hr. at room temperature, at the conclusion of which the mixture is filtered. The filtrate and the untreated, contaminated water previously set aside are cultured as set forth above under "Biocide Test." After incubation, the plates are counted and the differences noted. As a result, it is concluded that treatment of the water with the stripped, spent catalyst reduced the *E. faecium* content of the water.

EXAMPLE 9

Stripped, Spent Silver Catalyst as a Surface Protectant

A coating is formulated by combining 100 g boiled linseed oil and 50 g of the powdered, stripped, spent catalyst of Example 7. The resulting mixture is milled in a ball mill containing alumina milling media for a period of five days. The mixture is then recovered from the ball mill, and the stripped, spent catalyst remains homogeneously distributed in the linseed oil. A flat glass plate is coated on about one-third of its face with the linseed oil-based mixture, and on another one-third of its face with the pure boiled linseed oil. The coated plate is set aside for two weeks in a small oven maintained at about 80° C. At the end of this period, the coatings have hardened, and the glass plate is removed from the oven.

The glass plate is placed in a large Petri dish, and 25 ml of an aqueous culture containing $2 \times 10^6$ *E. Coli* microorganisms per ml is poured onto the coated side of the glass plate, flooding portions of both coatings as well as the uncoated one-third of the surface. The Petri dish is then covered. After being in contact with the surfaces for 30 min, pipettes are employed to transfer and culture 0.1 ml of the liquid from each third of the glass plate as set forth above under "Biocide Test." After incubation, the plates are counted and the differences noted, leading to the observations that the linseed oil coating which contained the stripped, spent silver catalyst inhibited the growth of *E. coli*, as compared to the uncoated surface, as well as the surface coated with pure linseed oil.

EXAMPLE 10

Stripped, Spent Silver Catalyst as a Paper Additive

A bundle of paper towels is sterilized in a steam sterilizer. Sterile towels are torn into small pieces, added to a flask containing sterile water and stirred vigorously for several hours until a homogeneous pulp containing about 30 percent solids is produced. The wet pulp is divided approximately in half. One portion of the pulp is made into a sheet of paper on a hand screen. To the other half portion of the pulp an amount of the powdered, stripped, spent silver catalyst of Example 4 above sufficient to constitute about 25 percent by weight of the combination of the dry paper plus spent catalyst is added, and a sheet of paper is produced from the mixture on the hand screen.

After drying the two sheets of paper at room temperature for two days under sterile conditions, each sheet is crumpled into a separate Erlenmeyer flask, 200 ml of a culture containing about $2 \times 10^6$ *E. coli* microorganisms per ml is added and the mixture, in each case, is allowed to stand for 24 hours. At the conclusion of this period, the supernatant liquid in each flask is cultured as set forth above under "Biocide Test." It is observed that the E. coli level in the culture derived from the flask containing the paper impregnated with the stripped, spent silver catalyst is lower than the *E. coli* level in the other culture.

Whereas, the method of this invention has been described by reference to the specific Examples set forth above, it is not intended that the invention be limited to those Examples. The invention is to be limited only by reference to the following claims.

I claim:

1. A method of controlling microorganisms which comprises contacting the microorganisms with a biocidally effective amount of a stripped, spent silver catalyst.

2. The method of claim 1 wherein the microorganisms to be contacted are contained in a fluid.

3. The method of claim 2 wherein the microorganisms are selected from the group consisting of bacteria and fungi.

4. The method of claim 3 wherein the microorganisms are bacteria selected from the group consisting of gram positive and gram negative bacteria.

5. The method of claim 3 wherein the microorganisms are bacteria selected from the group consisting of *E. coli* and *E. faecium*.

6. The method of claim 5 wherein the fluid is water.

7. The method of claim 6 wherein the water is contained in a municipal water system.

8. The method of claim 6 wherein the water is contained in aqueous effluent discharged from a sewage treatment plant.

9. The method of claim 6 wherein the water is contained in a cooling tower water recirculation system.

10. The method of claim 6 wherein the water is contained in condensate from an air conditioning system.

11. The method of claim 6 wherein the water is contained in a swimming pool water recirculation system.

12. The method of claim 6 wherein the water is contained in a hot tub water recirculation system.

13. The method of claim 1 wherein the stripped, spent silver catalyst is carried in a coating which covers a surface on which the growth of infectious microorganisms is to be controlled.

14. The method of claim 1 wherein the stripped, spent silver catalyst is incorporated into a product in and on which the growth of infectious microorganisms is to be controlled.

15. The method of claim 14 wherein the product is paper.

16. A method of controlling microorganisms which comprises contacting the microorganisms with a biocidally effective amount of a stripped, spent silver catalyst wherein the stripped, spent silver catalyst comprises approximately less than 0.1 percent silver by weight.

17. The method of claim 16 wherein the microorganisms contacted are contained in a fluid.

18. The method of claim 17 wherein the fluid is water.

19. The method of claim 16 wherein the stripped, spent silver catalyst is carried in a coating which covers a surface on which the growth of microorganisms is controlled.

20. The method of claim 16 wherein the stripped, spent silver catalyst is incorporated into a product in and on which the growth of microorganisms is controlled.

* * * * *

UNITED STATES PATENT AND TRADEMARK OFFICE
CERTIFICATE OF CORRECTION

PATENT NO. : 5,849,319

DATED : DECEMBER 15, 1998

INVENTOR(S) : Ronald F. Davies

It is certified that error appears in the above-identified patent and that said Letters Patent is hereby corrected as shown below:

Column 6, line 47, after the word catalyst cancel "." and insert - having a concentration of about 0.04 to less than 0.1 percent by weight of silver. -

Column 8 lines 2-3, cancel "approximately less than 0.1 percent" and insert - from about 50 to 900 ppm -

Signed and Sealed this

Twenty-third Day of March, 1999

Attest:

Q. TODD DICKINSON

*Attesting Officer*     Acting Commissioner of Patents and Trademarks